(12) United States Patent
Grim et al.

(10) Patent No.: US 6,461,317 B1
(45) Date of Patent: *Oct. 8, 2002

(54) WATER HARDENABLE COMPOSITIONS FOR SPLINTS AND BRACES

(75) Inventors: Tracy E. Grim, Tulsa, OK (US); Joseph M. Iglesias, Thousand Oaks, CA (US); Kelly M Speakes, Woodland Hills, CA (US); Michael Campos, Granada Hills, CA (US); Steven T. Pelote, Valley Village, CA (US)

(73) Assignee: Royce Medical Company, Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/857,082

(22) PCT Filed: Nov. 30, 1999

(86) PCT No.: PCT/US99/28346

§ 371 (c)(1),
(2), (4) Date: May 31, 2001

(87) PCT Pub. No.: WO00/33772

PCT Pub. Date: Jun. 15, 2000

Related U.S. Application Data

(63) Continuation-in-part of application No. 09/205,677, filed on Dec. 4, 1998, now Pat. No. 6,007,505, which is a continuation-in-part of application No. 09/088,905, filed on Jun. 6, 1998, now Pat. No. 6,139,513.

(51) Int. Cl.⁷ .................................................. A61F 5/00
(52) U.S. Cl. ................................................ 602/8; 602/6
(58) Field of Search ........................................ 602/5–8

(56) References Cited

U.S. PATENT DOCUMENTS

| | | |
|---|---|---|
| 3,043,298 A | 7/1962 | Brickman et al. |
| 3,373,741 A | 3/1968 | Hill et al. |
| 4,454,873 A | 6/1984 | Laufenberg et al. |
| 4,667,660 A | 5/1987 | Eingorn |
| 4,683,877 A | 8/1987 | Ersfeld et al. |
| 4,774,937 A | 10/1988 | Scholz et al. |
| 4,856,502 A | 8/1989 | Ersfeld et al. |
| 4,937,146 A | 6/1990 | Dull et al. |
| 4,947,839 A | 8/1990 | Clark et al. |
| 4,960,116 A | 10/1990 | Milner |
| 4,996,979 A | 3/1991 | Grim et al. |
| 5,166,480 A | 11/1992 | Böttger et al. |
| 5,250,344 A | 10/1993 | Williamson et al. |
| 5,334,442 A | 8/1994 | Okamoto et al. |
| 5,476,440 A | 12/1995 | Edenbaum |
| 5,603,691 A | 2/1997 | Scholz et al. |
| 5,738,639 A | 4/1998 | Cueman et al. |
| 6,007,505 A * | 12/1999 | Grim et al. ............ 602/5 |

* cited by examiner

*Primary Examiner*—Kim M. Lewis
(74) *Attorney, Agent, or Firm*—Oppenheimer Wolff & Donnelly LLP

(57) ABSTRACT

An orthopaedic support (50) or product is formed of a doubleknit type fabric material with spaced interwoven layers formed of high strength materials, and an open-work matrix of filaments or threads interconnecting the layers. The fabric may be impregnated with water hardened urethane. Hydroxy propyl methyl-cellulose (HPMC) will also be applied to the doubleknit type material or other casting fabric in sufficient amount to reduce the stickiness of the water hardened urethane. The HPMC may be mixed in with the water surfaces of the doubleknit type material. The orthopaedic support (50) or product is packaged in a water-vapor impermeable package; and is opened. Water is supplied to the fabric when it is applied to the part of the anatomy requiring support. The fabric may be included in a soft goods' support including a water distribution network, and straps (74) to hold the support in place.

19 Claims, 14 Drawing Sheets

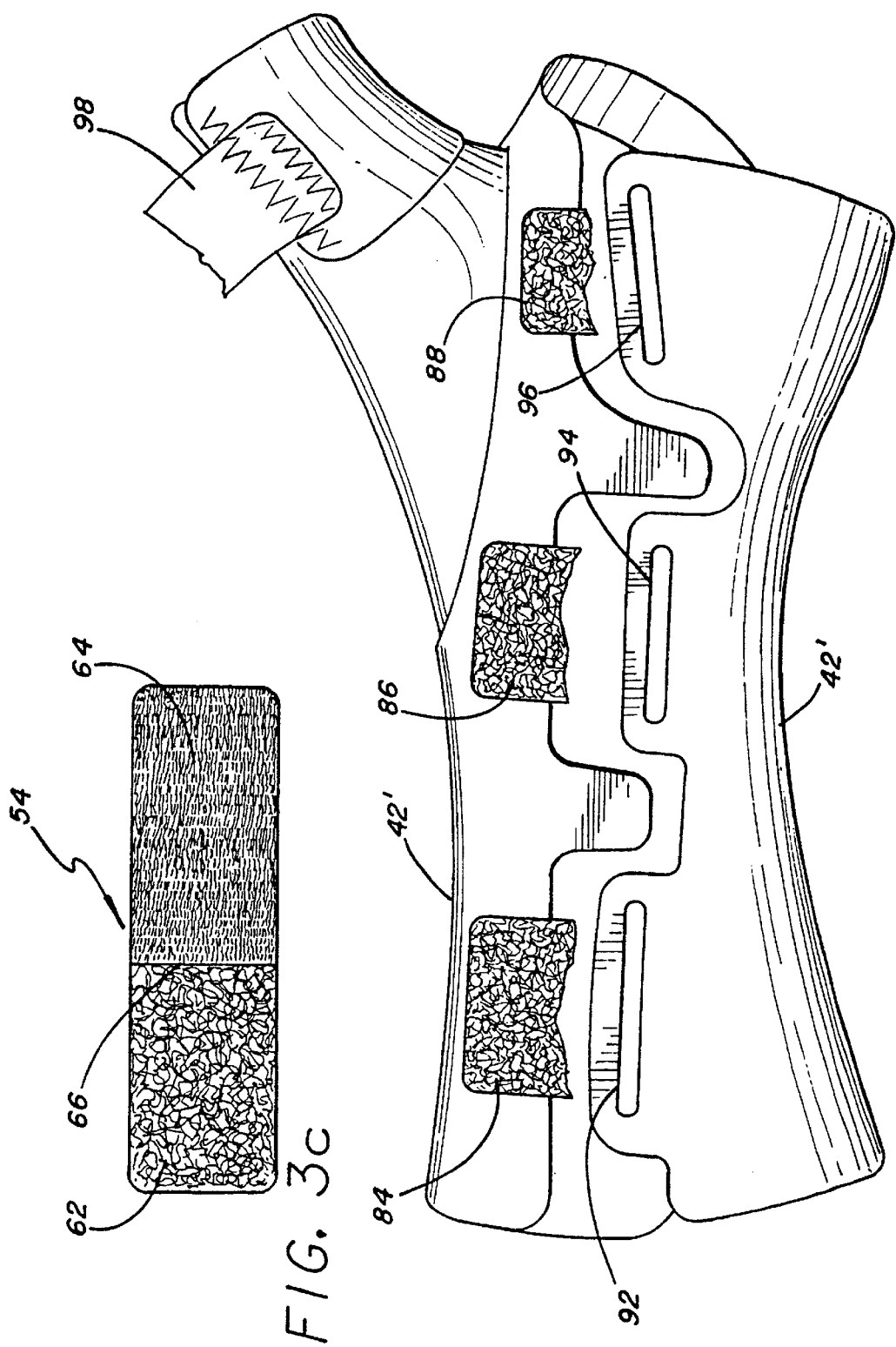

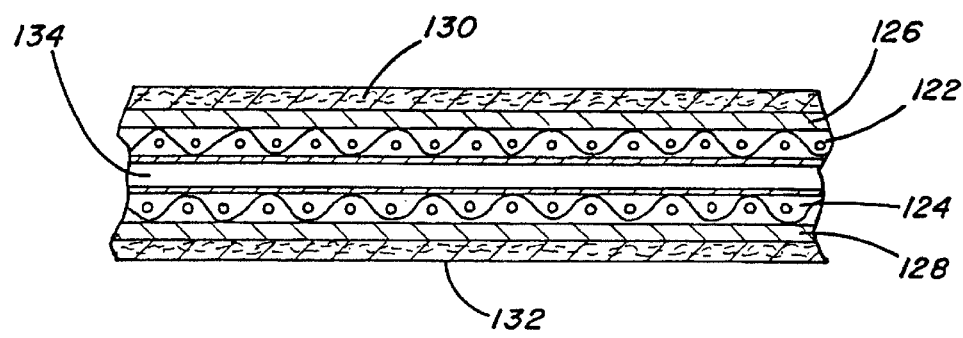
FIG. 10
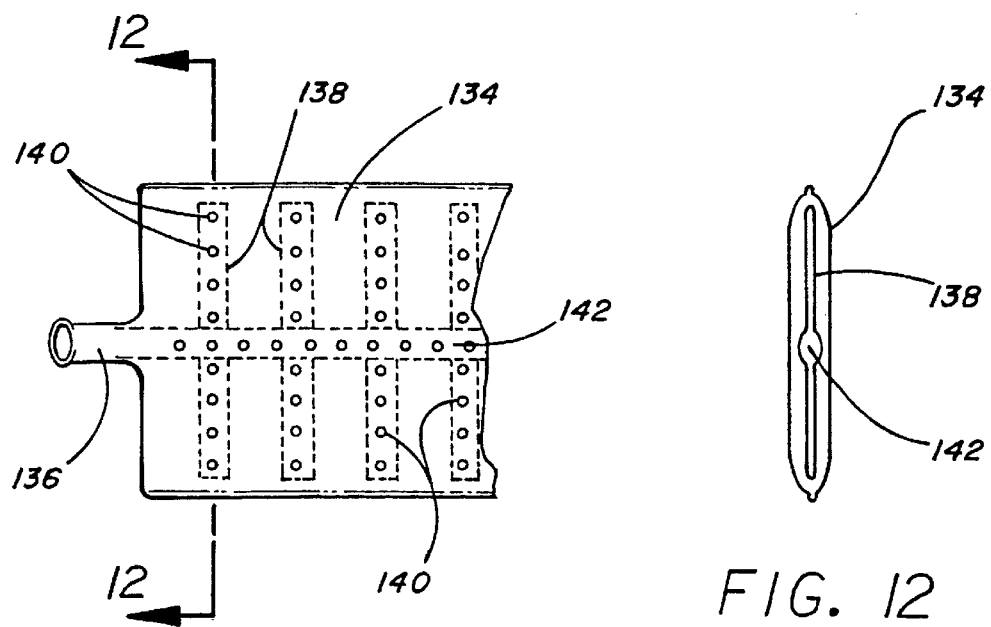
FIG. 11
FIG. 12

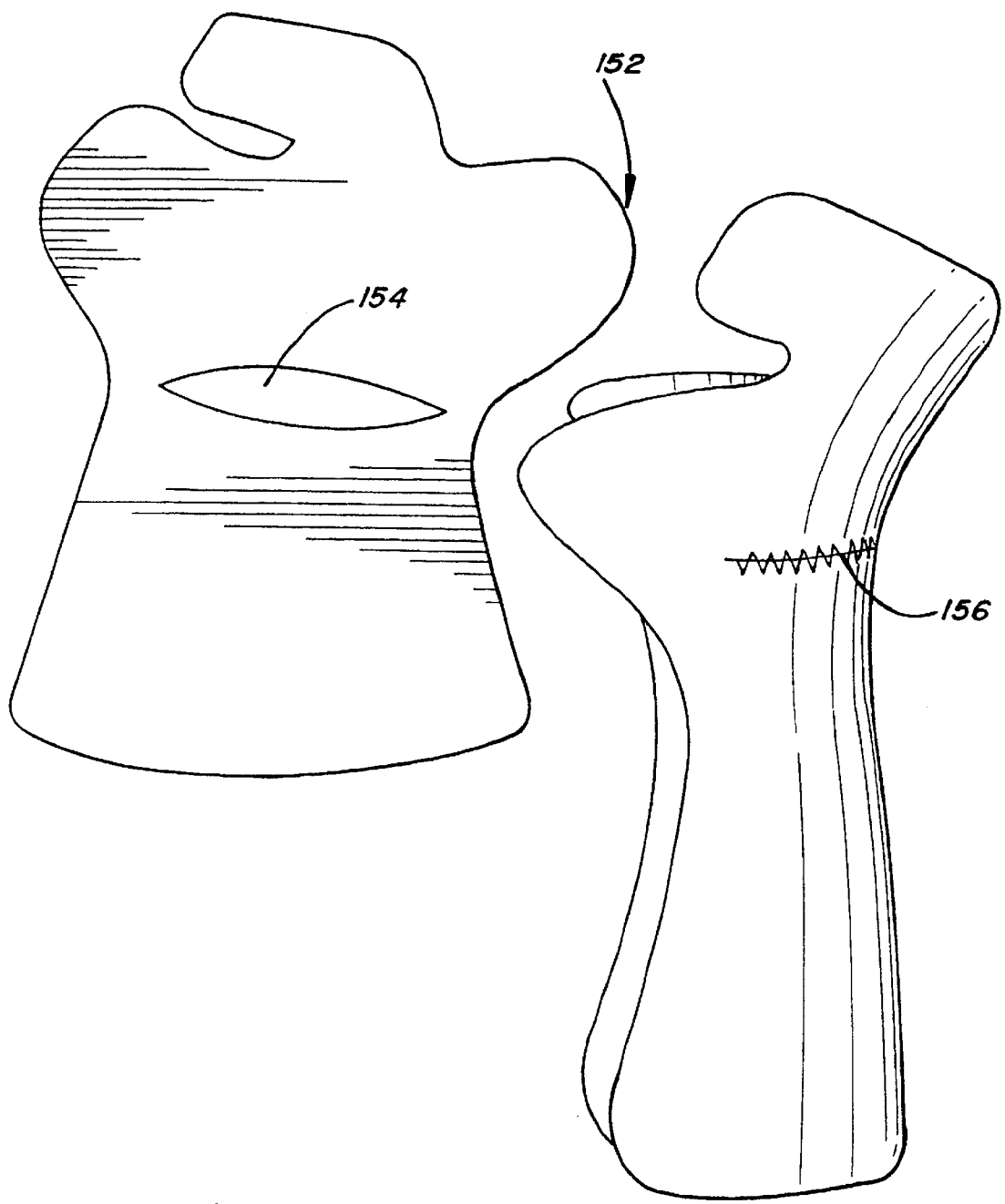

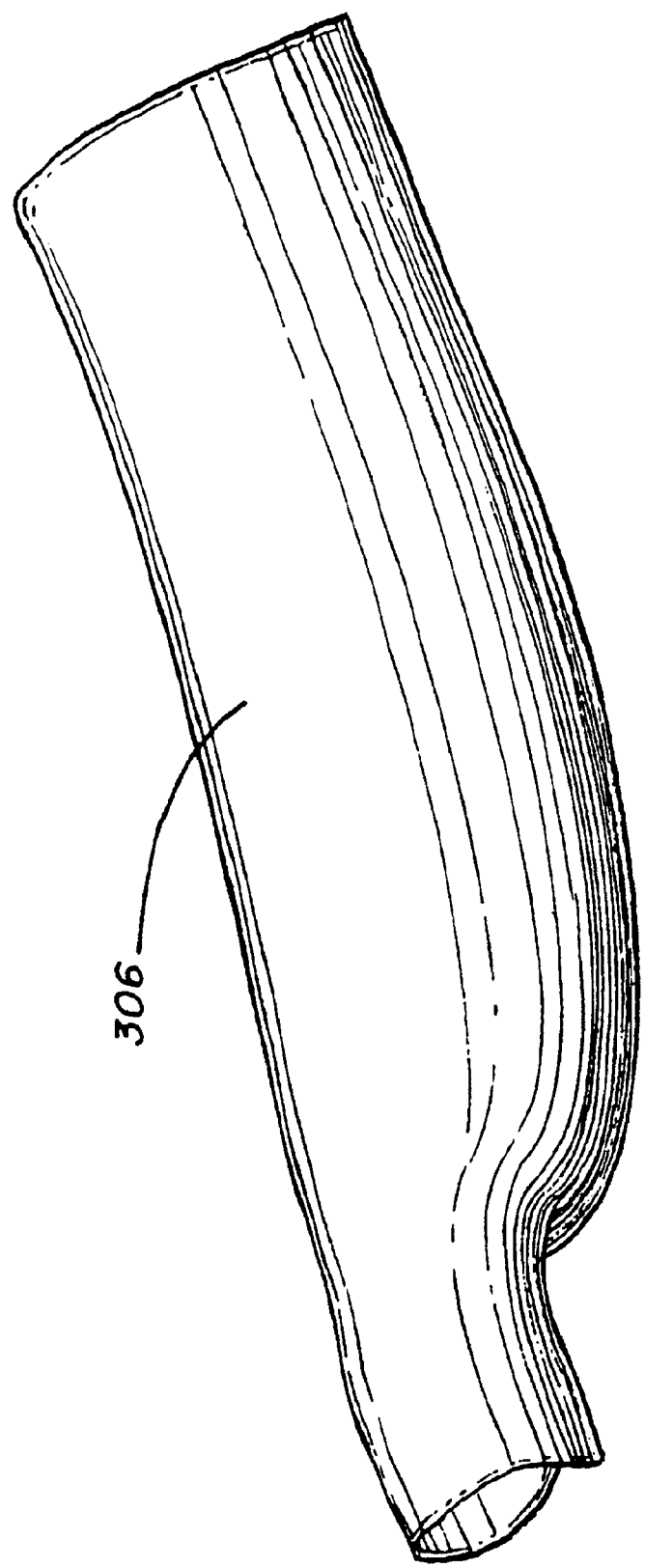

WATER HARDENABLE COMPOSITIONS FOR SPLINTS AND BRACES

RELATED PATENT APPLICATIONS

This specification is a continuation-in-part of U.S. patent application Ser. No. 09/205,677 filed Dec. 4, 1998, entitled "Tractable Orthopaedic Splint or Support," now U.S. Pat. No. 6,007,505, issued Dec. 28, 1999, which is a CIP of U.S. patent application Ser. No. 09/088,905, now U.S. Pat. No 6,159,513 assigned to the Assignee of this invention Jun. 6,1999.

FIELD OF THE INVENTION

This invention relates to water hardenable orthopaedic splints and supports.

BACKGROUND OF THE INVENTION

In the formation of casts, it is useful to use a water hardenable material, such as Plaster of Paris or a water hardenable urethane, as disclosed for examples in U.S. Pat. No. 3,373,741 or in German Offenlegenschrift No. 2,651, 089.

With regard to the construction of water hardenable casts, plaster of paris casts have been used for many years. They normally involve the use of several layers of cotton "skrim" or a very loosely woven cloth using thin threads and having large openings, and these layers of cloth are embedded in plaster of paris. In use, strips of the skrim and plaster of paris are dipped in water and wrapped around the injured portion of the anatomy. Normally padding is employed next to the skin to protect from the hardening cast material. As the plaster of paris hardens, it is somewhat exothermic, but there is no gas released. U.S. Pat. No. 3,043,298 (Brickman, et al.) assigned to Johnson & Johnson, discloses the addition of hydroxypropyl methyl-cellulose (HPMC) to a Plaster of Paris bandage to be used as an orthopaedic cast which gives the Plaster of Paris a creamy and viscous consistency or texture when wet with water just prior to application. More specifically, a plain Plaster of Paris cast without additives has a somewhat granular texture, akin to wet sand, while with the addition of HPMC it is somewhat smoother in texture with a consistency similar to mud or smooth clay.

Concerning water hardenable urethane casts, they are usually formed of a high strength fabric which may be 1/16 of an inch or so thick, and which is normally knitted so that there are small visible openings through the fabric. The water hardenable urethane material is impregnated into the fabric. At the time of use, assembly may be dipped in water prior to application to the injured part of the anatomy. Again, padding is usually employed to protect the skin from the cast material. In the case of urethane, the exothermic hardening reaction is accompanied by the release of carbon dioxide, and the wet urethane is very sticky. With the outgassing of the $CO_2$ and the resulting bubbling out of the urethane material, the warm sticky assembly would be difficult for the doctor or orthopaedic technician to handle, and properly apply to the patient. One technique directed to overcoming this problem is disclosed in Mathew T. Scholz, et al. U.S. Pat. No. 4,667,660 and U.S. Pat. No. 4,774,937. As disclosed in these patents, the coefficient of friction of a curable resin sheet may be reduced by using either a lubricant of a certain type bound to the resin, and/or by using additive lubricants which are either (a) polysiloxanes, (b) surfactants, and polymers consisting of hydrophilic groups of certain types. It was the considered view of knowledgeable persons in the orthopaedic field that the techniques as described in the Scholz, et al. patents were the only practical way of obtaining the desired low coefficient of friction where water hardenable urethane materials were employed. Thus, for example, the assignee of the Brickman patent cited above, apparently employed the lubricants of the Scholz, et al. patents for its hardenable urethane cast assemblies, see *Minnesota Mining and Manufacturing Co. v. Johnson & Johnson*, 24 U.S.P.Q.2d 1321, 976 F.2d 1559 (CAFC 1992).

With regard to aspects of the invention emphasized in U.S. patent application Ser. No. 09/088,905 cited above, it has previously been proposed to use water-hardenable materials in orthopaedic supports and casts; and typical patents disclosing such products include U.S. Pat. No. 4,996,979, granted Mar. 5, 1991, and U.S. Pat. No. 4,683,877, granted Aug. 4, 1987. However, when materials as disclosed in these patents are employed, the flow of liquid through the open cell foam or layers of fabric, as well as the strength of the orthopaedic support may not be subject to the desired level of control.

It is also noted that these prior art products mentioned above have other problems. Thus, for example with regard to the casts or supports using layers of material, care must be taken to firmly engage the layers during the setting period to ensure unitary bonding of the entire layered cast or assembly. Doctors practicing in this area even have a saying: "rub it like you love it," to encourage full engagement of the layers during hardening of the water-hardenable material. This step obviously requires care and expertise, as it is undesirable to apply undue force to an injured limb involving broken bones, for example. Further, if this technique is not properly employed, the layers will not fully bond together, and the cast or support will be weak, and the layers could separate. Also with regard to the hardenable splints or supports using open cell foam, they may lack sufficient flexibility and conformability to properly fit the three-dimensional parts of the anatomy requiring splinting or support.

Fiat rigid panels have also been proposed using double-knit fabrics and hardenable resins, as indicated by U.S. Pat. No. 5,166,480, granted Nov. 24, 1992, and entitled "Knitted Fabric Panel Structure and Process of Manufacture." Attention is also directed to U.S. Pat. No. 5,334,442, granted Aug. 2, 1994. This patent discloses an intermediate pliant sheet which may be made of a single layer fabric such as a fiberglass fabric impregnated with a water-hardenable material. Then, on both sides of this pliant layer, the patentees disclose the use of layers of doubleknit material. Thus, with doubleknit material present in the assembly, it is not used to receive the water-hardenable material but is only used for padding.

As noted above, prior art orthopaedic products have involved shortcomings in the flow control of water to the water-hardenable material and the strength of the orthopaedic device.

SUMMARY OF THE INVENTION

It is an important object of the present invention to provide an orthopaedic splint or support which is smooth and is not rough so that it could catch on clothing or the like; and which is also smooth and velvety as it is being applied and molded to the injured member of the patient, while concurrently providing a strong layer-to-layer bonding when overlapping layers of the casting material are used.

In accordance with one specific illustrative embodiment of the invention, the foregoing object is achieved through the use of high strength fabric, preferably doubleknit type material impregnated both with water hardenable urethane and also with HPMC. Without the HPMC, following water immersion, the urethane becomes very sticky and-has an exothermic reaction accompanied by the release of carbon dioxide ($CO_2$) and the result is a bubbly, sticky assembly which is very difficult to work with. However, the addition of the HPMC acts as a controlling agent for the assembly and, in the case of casting tapes, permits easy handling and wrapping of the layers of the casting tape, and facilitates controlled bubbling of the $CO_2$ through the layers of tape, ensuring layer-to-layer bonding of the urethane impregnated layers of tape, to form a high strength cast. Further, the final cast is remarkably smooth and free of the coarse and rough outer surfaces characteristic of synthetic casts made in accordance with the patents cited hereinabove.

In practice, the HPMC is supplied in powder form and contains a small percentage, such as 1%, content of water. Because the hardenable urethane is water sensitive, this would normally be considered to be a negative factor, as the manufacturing process is carefully controlled to eliminate moisture and maintain very low humidity conditions. The HPMC does not dissolve when admixed with the urethane chemistry, but simply becomes encapsulated within the viscous resin. In the course of coating the urethane resin combination onto the supporting fabric, it may be thoroughly mixed to avoid separation as it is coated. Also, because the HPMC stays in powder form, the level or amount of rubbing of the material following water activation controls the physical properties of the cast or splint. More specifically, the tackiness and slipperiness of the assembly is determined by the amount of rubbing as the HPMC becomes somewhat gelatinous when contacted by water. Accordingly, if the doctor or medical technician who is applying the splint or support does not want very slippery material, he would merely not rub the cast or splint very much. The more the assembly is rubbed, the more the HPMC is exposed to water, and the coefficient of friction is further reduced.

It is further noted that as the cast or splint dries, the HPMC loses its slippery nature quickly as compared with silicone/urethane resin combination used in certain prior art products, and the resultant layered splints or casts are stronger and are more resistant to "peel" or the delamination of adjacent bonded layers.

The HPMC allows the HPMC/resin assembly to foam and swell, thereby promoting a creamier texture to the urethane. We therefore have a much smoother cast on the surface. This is desirable because prior art urethane resin casts were very porous and had a rough surface due to the surface of the lightly coated fiberglass fabric becoming hard and abrasive like a metal screen. Because our HPMC reacts with water, we can enjoy a smoother surface by simply allowing the chemistry to become gelatinous, then smoothing the creamy material by simply rubbing the surface of the outer layer. The result is better for the patient. A smoother cast surface means less rubbing against adjacent clothing during the daytime and less rubbing against adjacent skin or a partner's skin during sleep. Also it is more comfortable for the skin of the fingers which come in contact with the cast throughout the full rehabilitation period using certain cast configurations. For example, in the case of an arm and wrist cast, or thumb spica cast, or an ulnar gutter cast, immobilization near the fingers for four to six weeks at a time, the friction with and possible irritation of adjacent fingers is a significant factor.

Returning to the advantages as compared with prior art water hardenable urethane casts, in those prior art systems the use of silicone or other similar additives, which always retain their slippery qualities, can reduce the strength of the completed cast or splint by reducing inter-laminar strength; and, in addition, an element of control of this level of slipperiness or the coefficient of friction, is lost.

It is also noted that the BPMC has a tendency to initiate foaming in the urethane resin after both are activated by water. Further, it was noted that HPMC has the effect of initiating better lamination of the cast/splint. In fact, it has been noted that it works in combination with the off-gassing which is a natural byproduct of the water-activated resin. Because the HPMC increased the creaminess of the resin after activation by water, it appears to be "carried" by the off-gassing into adjacent layers resulting in (a) stronger lamination, and (b) less need to rub the cast in order to initiate interlamination bonding. This results in reduced skill requirements for the applicator. HPMC as combined with the urethane resin not only makes the product slippery (when exposed to water), it also promotes foaming and swelling of the chemistry which mechanically initiates a flowing of the resin from one layer into another aided by the off-gassing of the reacting resin. It is understood that the bursting bubbles have a tendency to "move" the resin into the holes and structure of the adjacent fabric layers, increasing laminate bonding.

Accordingly, a broad aspect of the invention involves the use of HPMC and a water hardenable resin applied to a fabric to provide an improved high strength casting or splinting material which may be used in tape form with improved lmaination strength, or in blanks for single layer usage.

In one preferred embodiment, the HPMC may be applied to the surface of the resin, while in other embodiments it may be mixed into the resin, for example, in powdered form.

The following paragraphs relate to aspects of the invention included in Ser. No. 09/088,905, cited hereinabove.

Accordingly, a principal object of the present invention is to improve both the control of the flow of water to the curable resin in orthopaedic supports or splints, and concurrently to provide the desired strength for the product.

Additional objects include increasing the reliability and simplifying the application, increasing conformity, reducing the thickness and weight while increasing the strength of casting materials.

In accordance with a method for forming an orthopaedic support illustrating the principles of the invention, an integral double layer fabric with a central open-work matrix, such as a doubleknit material, is employed to form a water hardenable splint or cast. The central open-work matrix includes integrally fabricated filaments or yarns which extend back and forth between the upper and lower fabric layers. This doubleknit type material is impregnated with a water-hardenable material under low humidity conditions, and is packaged in a water-vapor impermeable package. The impregnated doubleknit type material is located adjacent the injured portion of the anatomy, such as a broken bone, so that the material conforms to the desired configuration of the injured part of the anatomy. Water is applied through the open-work matrix of the doubleknit material to rapidly wet the water-hardenable material, to cause stiffening of the orthopaedic support and preventing undesired movement of the injured part. Water is applied to the doubleknit type material prior to application to the anatomy in the case of tapes and flat splinting shapes; and in the case of soft goods type products, following application of the soft goods support to the anatomy.

The orthopaedic support preferably includes high strength material such as glass fiber fabric, keviar fibers, aramids, or other high strength fibers, to provide strength to complement the rigidity or stiffness of the water-hardenable material.

The orthopaedic support using the doubleknit type fabric with its open-work central matrix may take a number of forms, including a tape, a flat or contoured splint shape configured to fit an injured portion of the anatomy, or a soft goods product having straps to secure the support in place, and having the doubleknit fabric within its construction.

Regarding the soft goods type support, it may be similar to that showing in U.S. Pat. No. 4,996,979, and may include either a single layer of impregnated doubleknit type fabric, or a plurality of such layers, with one or more intermediate water distribution networks. In addition, the soft goods support may include one or more of the following additional features: (1) an outer semi-flexible or semi-rigid member of plastic or the like to provide a general shape to the assembly prior to hardening of the material; (2) water impermeable layers for confining the water; (3) soft cloth lining material for engaging the skin of the injured party; and (4) straps for holding the assembly onto the injured part of the anatomy.

Incidentally, regarding water-hardenable materials and other matters, the disclosure of U.S. Pat. No. 4,996,979 is hereby incorporated into this specification by reference.

It is further noted that hardenable casts and splints formed of appropriate doubleknit type material have higher strength than the prior art foam or multi-layer hardenable splints.

Concerning the coefficient of friction of the various casting materials as discussed above, the following experiment was conducted, in accordance with ASTM Standard Test Method Designation D-1894-95. In the tests, samples of the various casting materials were immersed in water. Fifteen to eighteen seconds subsequent to removal, a stainless steel sled is gently placed on each sample and is then pulled across the sample. The coefficient of friction equals the force required to pull the sled divided by the weight of the sled.

Employing these test conditions and taking several readings during each test, the kinetic coefficient of friction of a commercial embodiment of a product as disclosed in the Scholz patent was about 0.31; and the coefficient of friction of one illustrative embodiment of the present invention, including the doubleknit material, water hardenable urethane and the HPMC, was approximately 1.76.

Furthermore, measurements of the surface roughness or deviation from flatness were also taken for the various cast materials. The surface roughness or deviation from flatness is the estimated depth of recesses of irregularities from a straight line or a flat plane in areas where the cast or splint is substantially flat. The surface roughness or deviation from flatness of the plaster of paris cast as disclosed in Brickman was approximately 0.015 to 0.025 inch; the surface roughness of a Scholz cast was about 0.035 inch; and the surface roughness of one illustrative embodiment of the present invention was generally less than 0.010 inch.

BRIEF DESCRIPTION OF THE DRAWINGS

FIG. 3B is a view of an alternative fiberglass soft goods device illustrating the principles of the invention;

FIG. 3C shows a strap using hook and loop type material, which may be employed in the orthopaedic soft goods products of FIGS. 3A and 3B;

FIG. 10 is a cross-sectional view of a multi-layer construction involving two layers of doubleknit material, a central water distribution network, outer water impermeable layers, and cloth fabric on the outside of the assembly;

FIG. 11 is a schematic view of a water distribution network included as a central portion of the assembly of FIG. 10;

FIG. 12 is a cross-sectional view taken along lines 12—12 of FIG. 11;

FIG. 13 is a flat blank including a cutout area to help in forming the blank into a cast or support for the thumb;

FIG. 14 shows the blank of FIG. 13 formed into a three-dimensional configuration for application to the forearm and thumb of a patient;

FIG. 21 shows an example of a hardened tractable orthopaedic splint or support in accordance with the present invention.

DESCRIPTION OF THE PREFERRED EMBODIMENTS OF THE INVENTION

Figure 1:
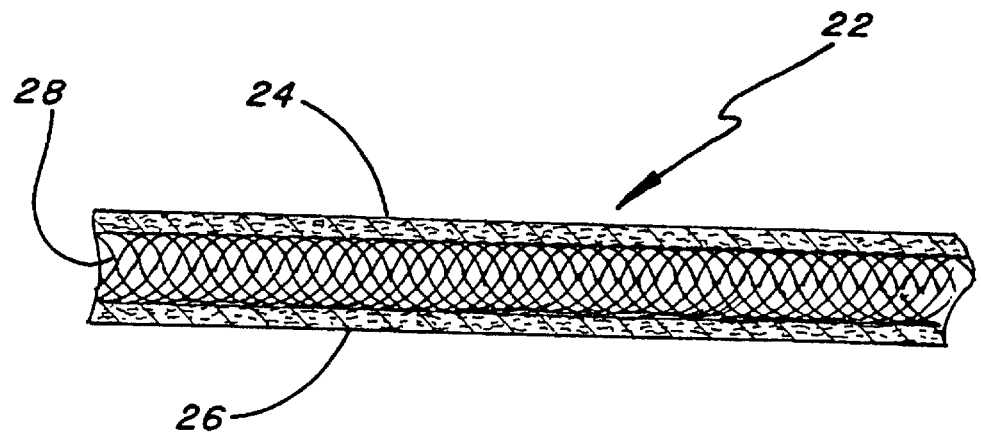
FIG. 1 is a cross-sectional view of a doubleknit type material which is to be employed in the fabrication of orthopaedic splints or supports in accordance with the present invention.

Referring more particularly to the drawings, FIG. 1 shows a doubleknit fabric 22 including the surface knits 24 and 26 and spacer yarns 28. The surface knits 24 and 26 can be of the same or different knit patterns. These patterns can range anywhere from smooth, essentially continuous surfaces to meshes and other more complex knits. They may be knit from materials such as polyester, nylon, and various aramid fibers, including fiberglass. The spacer yarns 28 keep the surface knits a specific distance apart, and allow for individual surface movement. They are usually composed of monofilament yarns, but can also be of multi-filament yarns. The spacer yarns 28 typically are made from polyester, nylon, or other thermoplastic materials that can be drawn into a yarn of the desired diameter. In addition, they may be made from glass and other aramid fibers.

Figure 2:
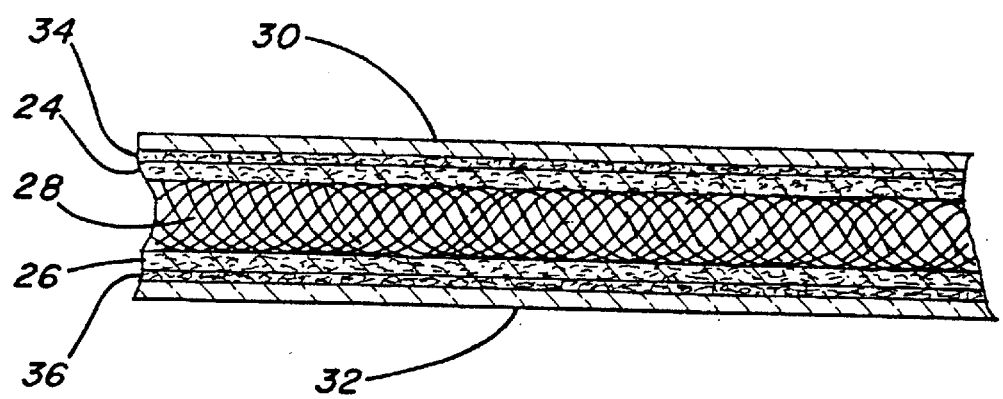
FIG. 2 is a cross-sectional view of a central layer of doubleknit material reinforced by layers of high strength material such as fiberglass fabric on both sides of the doubleknit material.

FIG. 2 shows how doubleknit materials may be reinforced with glass knits or other high strength fabrics to increase their strength. More specifically, fiberglass cloth material 30 and 32 may be bonded to the doubleknit material by adhesive webs 34 and 36. This bonding could also be achieved by any other known technique such as by flame bonding, or by sewing, for specific examples. The lamination of the glass knit fabrics 30 and 32 to the doubleknit material by the adhesive layers 34 and 36 also reduces the fraying of the glass knit when the assembly is cut, and holds the entire assembly intact during subsequent operations.

In an exemplary embodiment of the current invention, the doubleknit type material is used as a core in forming the orthopaedic device or material. The doubleknit type material is impregnated with a water hardenable urethane. Furthermore, a hydroxy propyl methyl cellulose (HPMC) additive is applied to the doubleknit type core.

Water hardenable urethane is known and has been used in prior orthopaedic devices. U.S. Pat. No. 4,996,979, issued to Grim et al., discloses detailed information regarding the use of unpolymerized urethane in soft-goods type, formable orthopaedic casts. However, when such disclosed materials are employed, the liquid flow through the layers of fabric or open cell foam and the strength of the orthopaedic support may not at the desired level of control. Furthermore, care and expertise are required to properly mold the hardenable splints layers during the setting period to ensure uniform bonding of the entire layered cast. Improper application would cause the layers to bond only partially together, causing the cast to be weak. Also, the hardenable splints or supports using open cell foam may lack sufficient flexibility and contormability to properly fit the three-dimensional injured parts of the anatomy that require splinting or support.

In practicing the present invention, there are several ways to apply HPMC to the doubleknit type material. As an example, HPMC may first be admixed with urethane in amounts of 1 to 10 parts by weight of HPMC per 100 parts by weight of the urethane. In the preferred practice, generally 4 parts by weight of HPMC per 100 parts by weight of urethane are used. Then, the HPMC and urethane mixture is used to impregnate the doubleknit type material to form an orthopaedic device or material. The doubleknit material, with its central openwork matrix formed by the spacer yarns, is ideally suited to initially receive the hardenable urethane and BPMC compound. As another example, the doubleknit type material may be initially be impregnated with water hardenable urethane. Then, HPMC may be applied to at least one outer surfaces of the doubleknit type material to form an orthopaedic device or material.

In forming a cast, the orthopaedic device or material may be mounted adjacent the portion of the anatomy to be supported. Water may then be applied to the orthopaedic device or material. The central openwork matrix of the doubleknit material makes the device or material ideal for receiving the water that is used to initiate the hardening and polymerization of the compound. Note that water can also be applied to the orthopaedic device or material prior to mounting the device or material. After the mounting of the device or material and the application of water, the device is hardened in place to conform to the configuration of the anatomy. The HPMC overcomes the stickiness of the urethane and makes the wetted assembly smooth and velvety, making it easy to conform the assembly to a patient's injured anatomy. Furthermore, the HPMC gives the hardened device a surface that is smooth and is not so rough such that it could catch on clothing, for example, or scrape the skin of the patient.

Figure 3A:
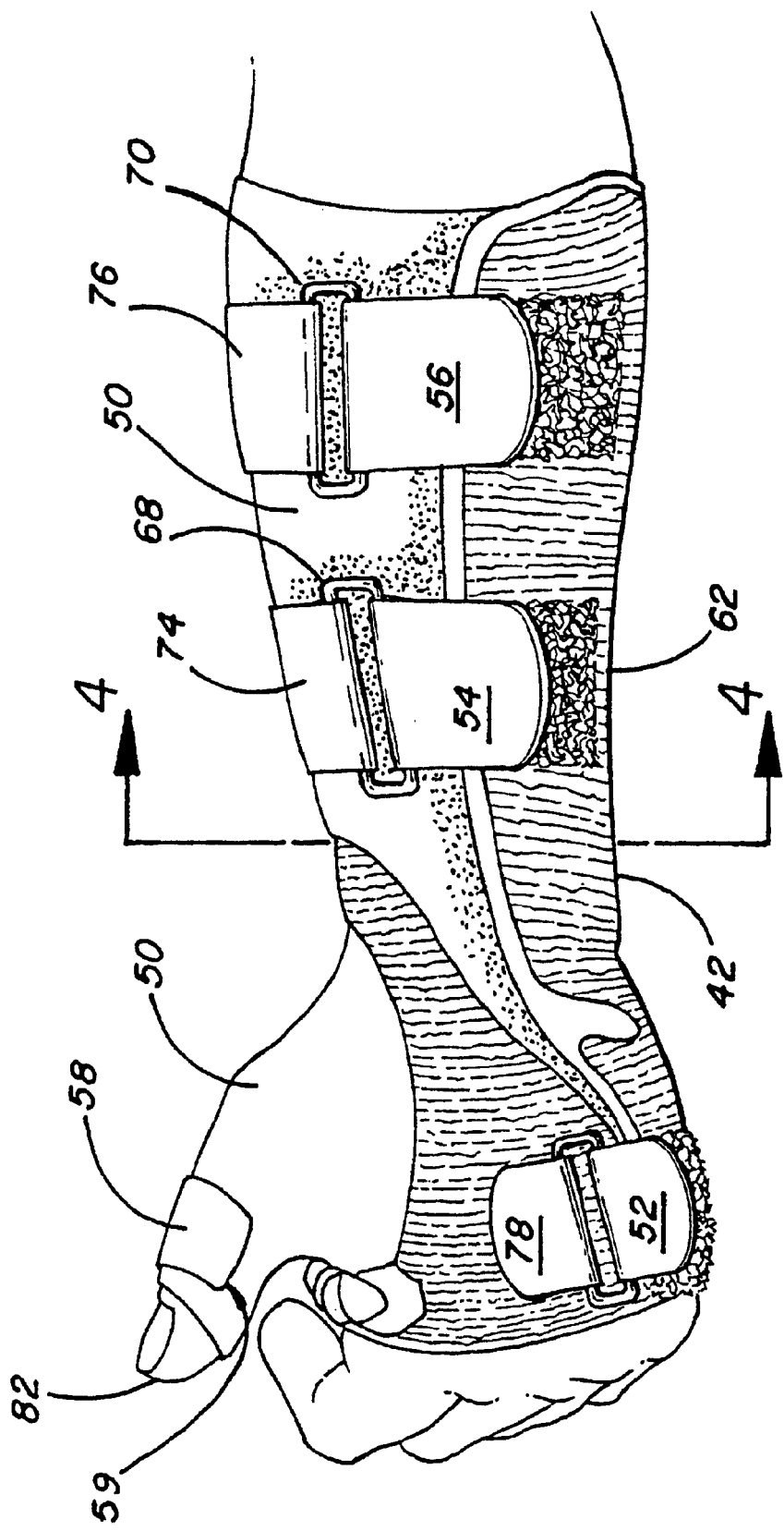
FIG. 3A is a side view of a fiberglass soft goods assembly for the forearm and wrist, employing a doubleknit fabric of the type shown in FIGS. 1 and 2.
Figure 4:
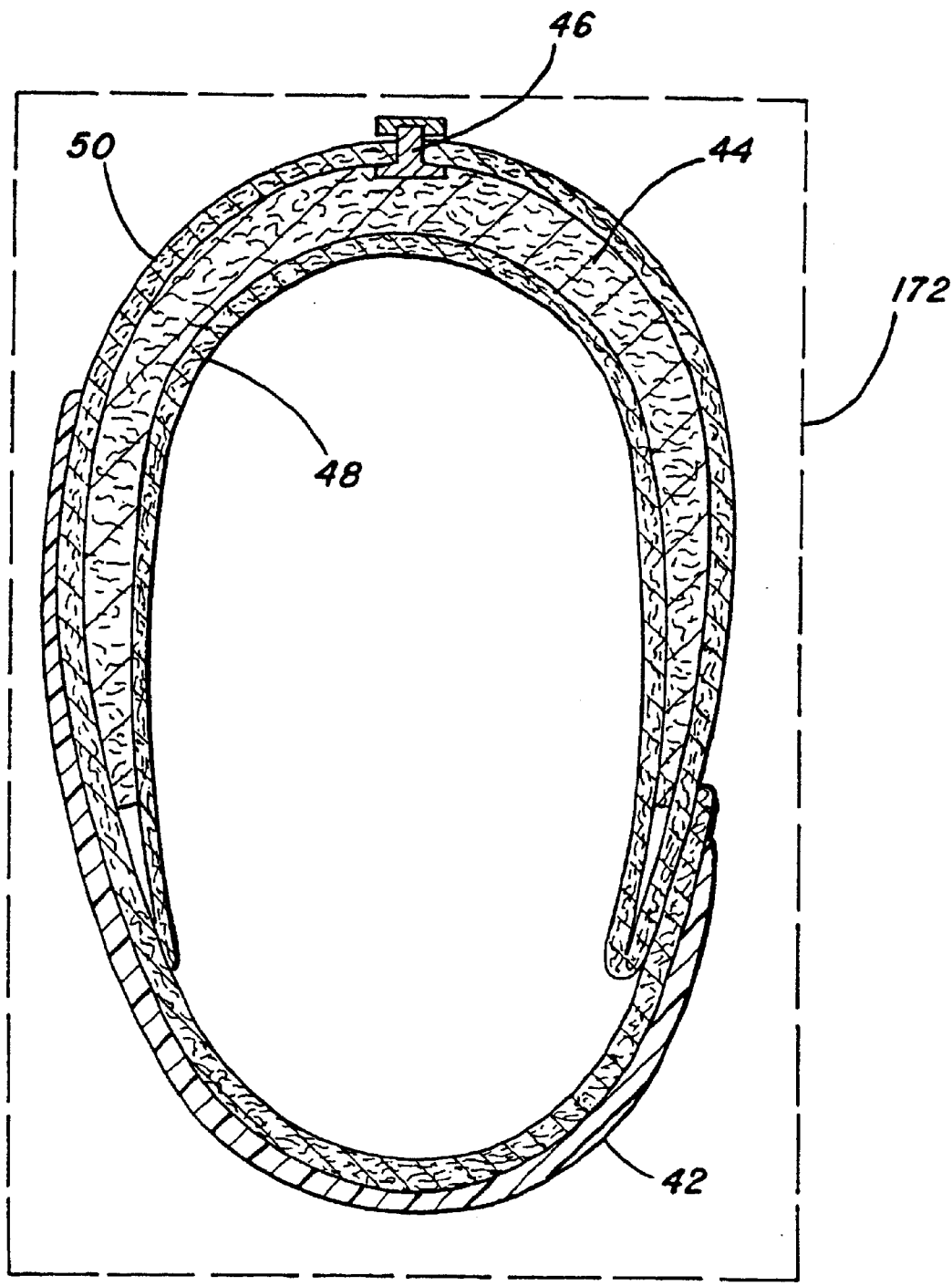
FIG. 4 is a cross-sectoinal view taken along lines 4—4 of FIG. 3A.

Reference will now be made to FIGS. 3A, 3B, and 3C, and FIG. 4 which is a cross-section taken along lines 4—4 of FIG. 3A. In FIGS. 3A, 3B, and FIG. 4, there is shown a shell-shaped or channel-shaped lower plastic member 42 which may be made of any semiflexible or semi-rigid plastic material, such as polypropylene, about $\frac{1}{16}$-inch in thickness. Mounted on the plastic channel member 42 is a layer of the doubleknit material assembly 44, 48, 50 which is impregnated with a compound of water hardenable urethane and HPMC. An inlet construction 46 is provided for receiving a standard or measured amount of water, in order to penetrate and activate the hardening of the urethane and BPMC compound impregnated in the doubleknit material 44. This can be provided by the use of a syringe having a needle which is inserted through the entry port 46. The first layer 48 and the second layer 50 of the assembly include both a water impermeable layer immediately adjacent the doubleknit material, and also a layer of cloth for comfortable engagement with the skin of the user and for providing a convenient surface for manipulating the orthopaedic support on its outer surface.

In addition to the materials mentioned in connection with FIG. 4 of the drawings, FIG. 3A shows four straps 52, 54, 56 and 58 which are employed to secure the orthopaedic device onto the forearm of the patient. These strap arrangements may extend from one edge of the channel member 42, to its other edge. The three straps 52, 54, and 56 have a configuration as indicated in FIG. 3C of the drawings. More specifically, strap 54, as shown in FIG. 3C of the drawings, includes a strip of loop type material 62 which is stitched together with a strip of hook type material 64. This type of hook and loop securing material is well known and is commonly sold under the trademark "VELCRO." The two straps may be held together in any desired manner by bonding or by the stitches 66, for specific example, as shown in FIG. 3C. In practice, referring back to FIG. 3A, one portion 62 having loop type material on its outer surface may be secured to the member 42 by adhesive or the like, and the free end 64 of the strap 54 extends up through the rectangular loop 68, and then back over the plastic member 42 to engage the hook type material on the lower surface of the strap 54 with the loop type material 62 of the strap. Incidentally, the rectangular loops 68, 70 and 72 are mounted on loops of the strap members 74, 76 and 78 which may be secured to the other edge (not shown) of member 42. Incidentally, the strap 58 has a simpler configuration and merely holds two portions of the layered material 50 together to provide proper support for the thumb 82 of the patient. The strap 58 and a matching area 59 on material 50 may be provided with mating hook and loop type material to adjustably maintain the strap in the desired closed position to restrain the thumb against excessive movement.

The embodiment of FIG. 3B is similar to that of FIG. 3A, and includes the plastic channel member 42' providing initial support, and the multi-layer material including the doubleknit central core, as indicated by the reference numeral 50 showing the outer surface of this multi-layer assembly. In the arrangements of FIG. 3B, the straps 84, 86 and 88 are shown broken away, but in use would extend through the integral loops 92, 94 and 96, respectively. The straps 84, 86 and 88 may be of the same type shown in FIG. 3C with exposed loop type material being secured to the plastic channel member 42', and the portion of the strap extending through the integral loops having mating hook type material on its surface. The strap 98, which is also shown broken away, serves to hold the thumb portion of the brace in its proper position to support the injured thumb and/or forearm of the user.

It is further noted in passing that the doubleknit type material as described herein may be substituted for the material shown at reference numeral 24 in FIG. 4 of U.S. Pat. No. 4,996,979, as cited hereinabove.

Figure 5:
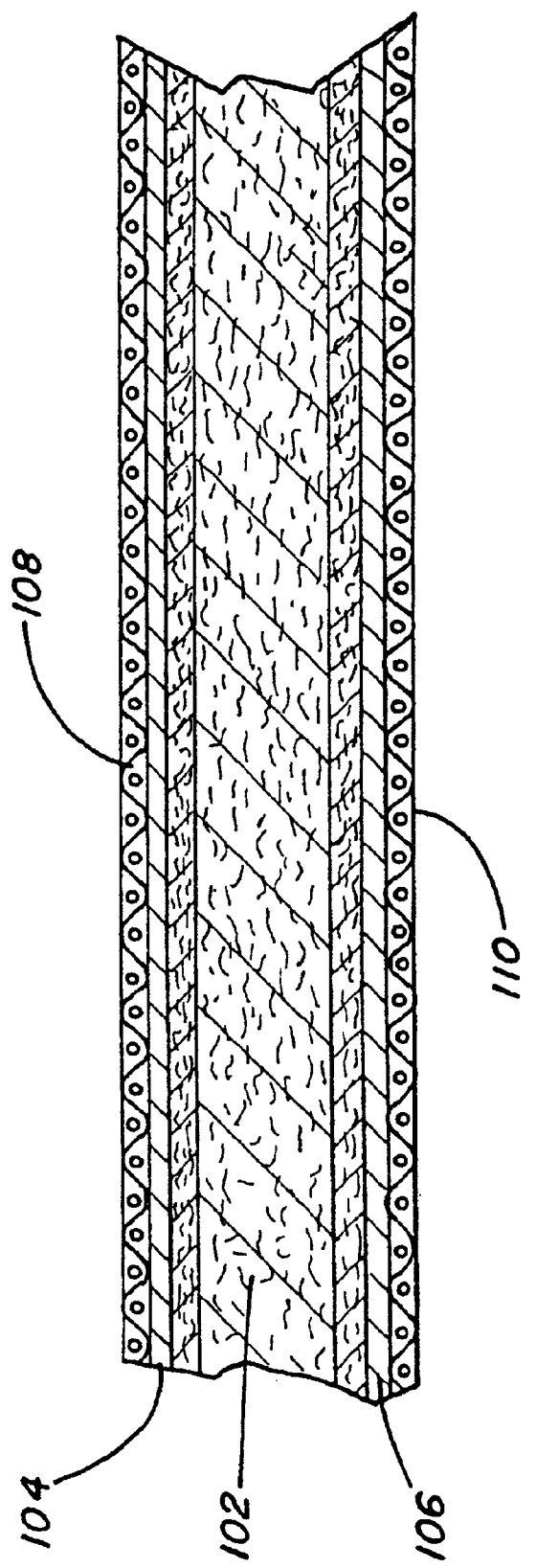
FIG. 5 is a cross-sectional view of an assembly including doubleknit material in the center, layers of water impermeable plastic, and finally an outer layer of cloth, which may be employed in the implementation of the present invention.

In the showing of FIG. 5, a central body of doubleknit material 102, with two outer surface knits, and a central matrix of spacer yarns is provided with an upper water impermeable plastic layer 104 and a lower water impermeable plastic layer 106 to retain water which is provided to the doubleknit material 102 and prevent it from touching the user, as well as confining the water action to the hardening of the impregnated material. In addition, outer cloth or fabric layers 108 on one side and 110 on the other side are provided for ease in handling the layered material and for comfort in engaging the skin of the user or patient.

Figure 6:
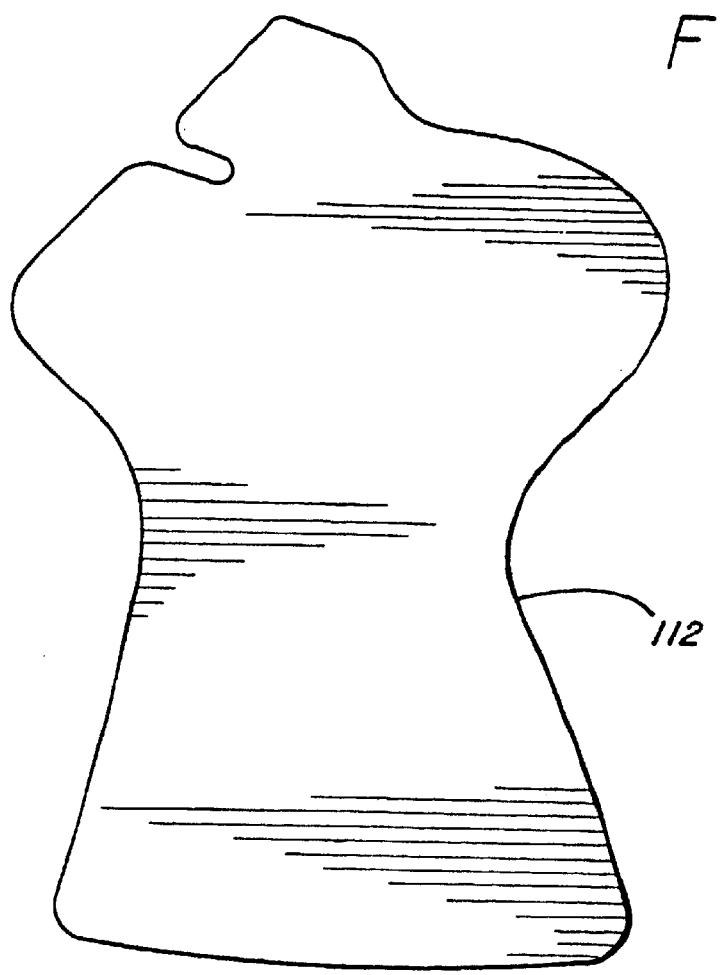
FIG. 6 shows a flat blank formed of the doubleknit material of the type shown in FIGS. 1 and 2.
Figure 7:
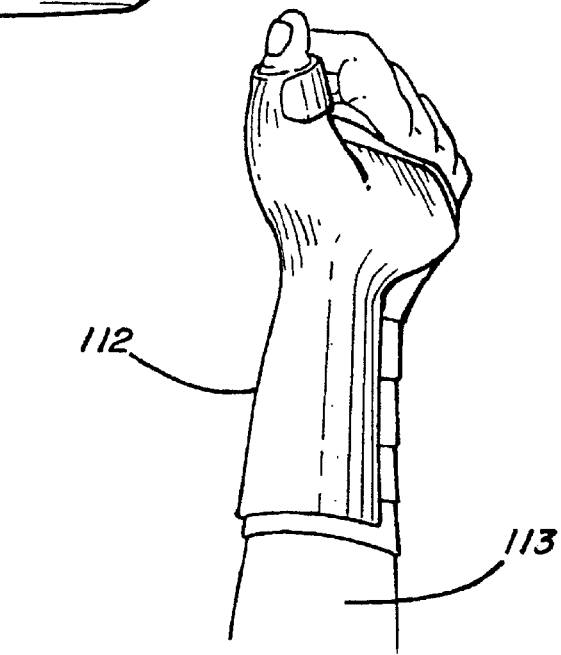
FIG. 7 shows the blank of FIG. 6 mounted on the forearm of a patient to provide supplemental support or splinting of this portion of the anatomy.

FIGS. 6 and 7 show, respectively, a blank 112 for providing splinting or casting action for the forearm 113 of a patient, and the blank 112 being mounted on the forearm 113. The blank 112 as shown in FIG. 6 is specifically configured to be mounted on the forearm, and may be held in place by appropriate elastic tape, or tape provided with hook and loop surfaces, for specific examples, once it is applied to the forearm of the patient. Of course, the blank is formed of the impregnated doubleknit material of one of the types described in the present specification, and is initially packaged in a water impermeable package.

Figure 8:
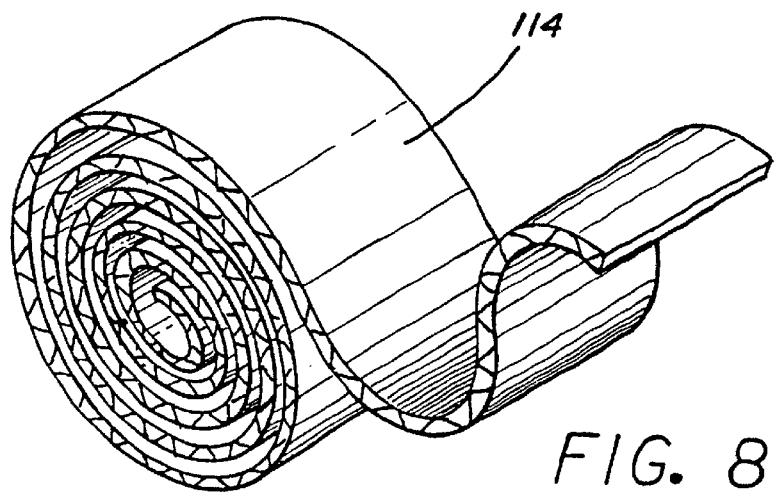
FIG. 8 is a perspective view of an orthopaedic casting tape formed of doubleknit material.
Figure 9:
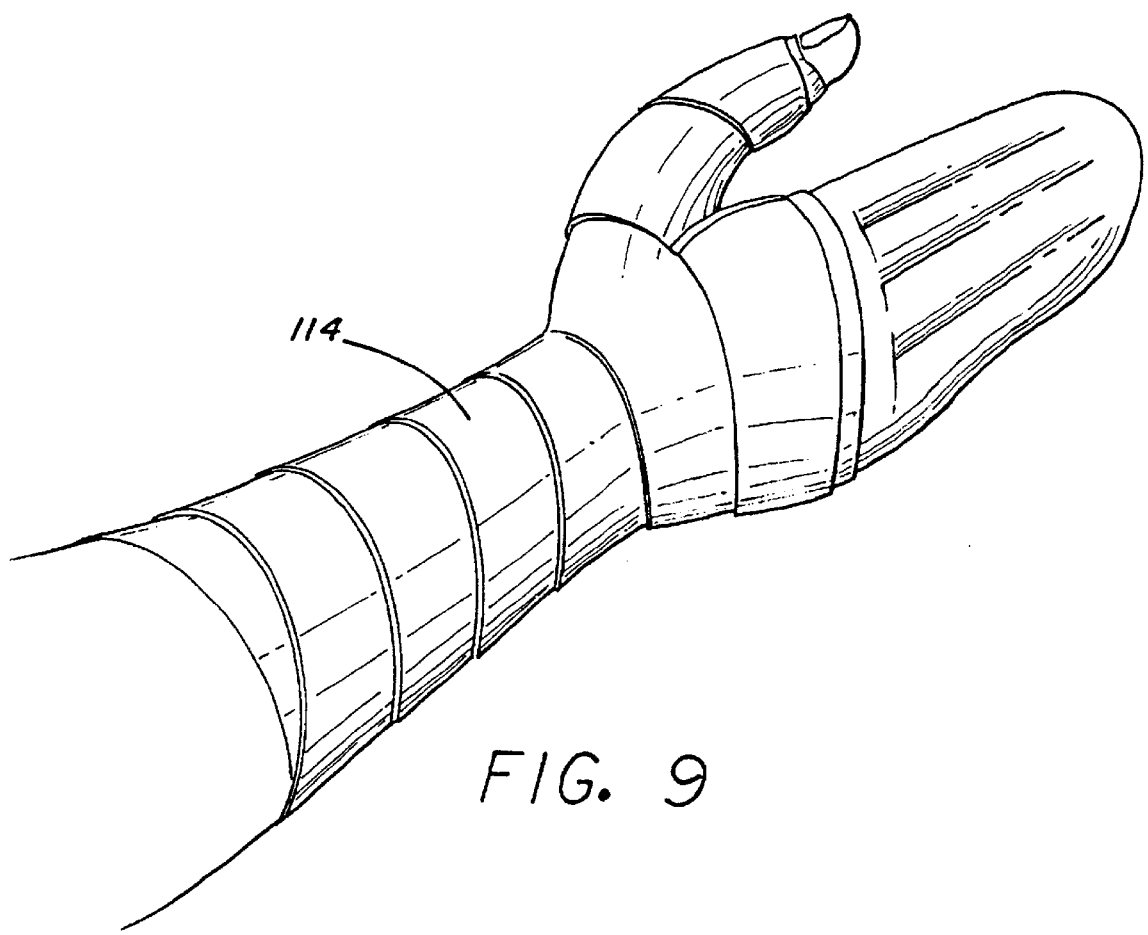
FIG. 9 shows the tape of FIG. 8 mounted on the forearm of a patient to provide casting or supplemental support.

FIG. 8 shows a tape 114 formed of impregnated doubleknit material; and FIG. 9 shows the tape of FIG. 8 applied to the forearm of a patient for splinting or support purposes.

FIGS. 10 through 12 show an alternative type of layering which may be employed, for example, in the fiberglass soft goods device of FIGS. 3 and 4. More specifically, the arrangement of FIG. 10 includes two layers of doubleknit material designated 122 and 124, an outer water impermeable layer 126 on one side of the assembly, and a water impermeable layer 128 on the other side, with outer fabric layers 130 and 132. A water distribution channel or network 134 is provided to direct activation water into the two impregnated doubleknit fabric layers 122 and 124.

FIGS. 11 and 12 show additional views of this water distribution network 134, with an inlet 136 which may be provided with a suitable one-way flapper type valve of a type known in this field, and distribution channels 138 with openings 140 for directing water throughout the two impregnated doubleknit fabric layers. FIG. 12 is a cross-sectional view of the thin walled water distribution network, with a central channel 142 and the branch channels 138.

FIG. 13 shows an alternative thumb-spica blank 152 with a die cut opening 154 extending through the thumb-spica blank. The opening 154 may be sewn up, as indicated in FIG. 14 by the stitches 156, or it may be left unstitched if desired. This provision of the opening is of assistance in forming the thumb-spica into its desired and necessary three-dimensional configuration as it is applied to the forearm of the patient, and avoids wrinkling or bunching up of the support blank.

Figure 15:
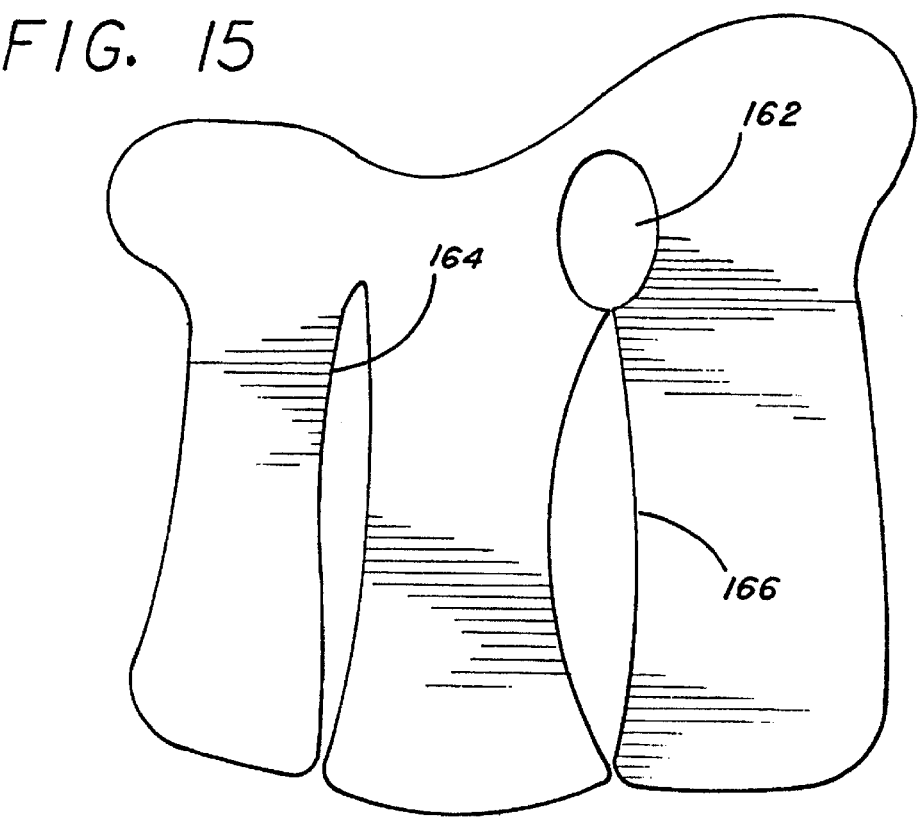
FIGS. 15 and 16 show a flat wrist brace with die cuts, and a corresponding wrist brace in a three-dimensional configuration, respectively.
Figure 16:
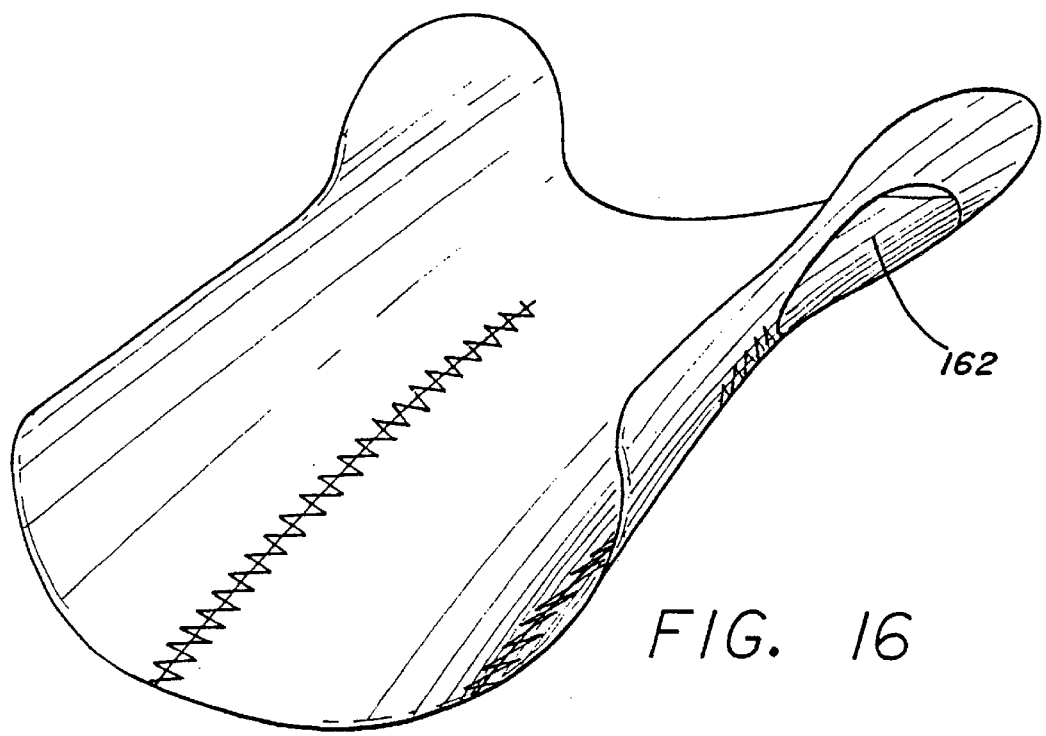

The wrist brace of FIG. 15 is similarly provided with die cut openings or slits 162, 164, and 166. Following stitching or otherwise bonding of the adjacent edges together, the wrist brace is formed into a three-dimensional configuration, as shown in FIG. 16. The opening 162 is to receive the thumb of the patient to assist in locating the wrist brace on the forearm.

Figure 17:
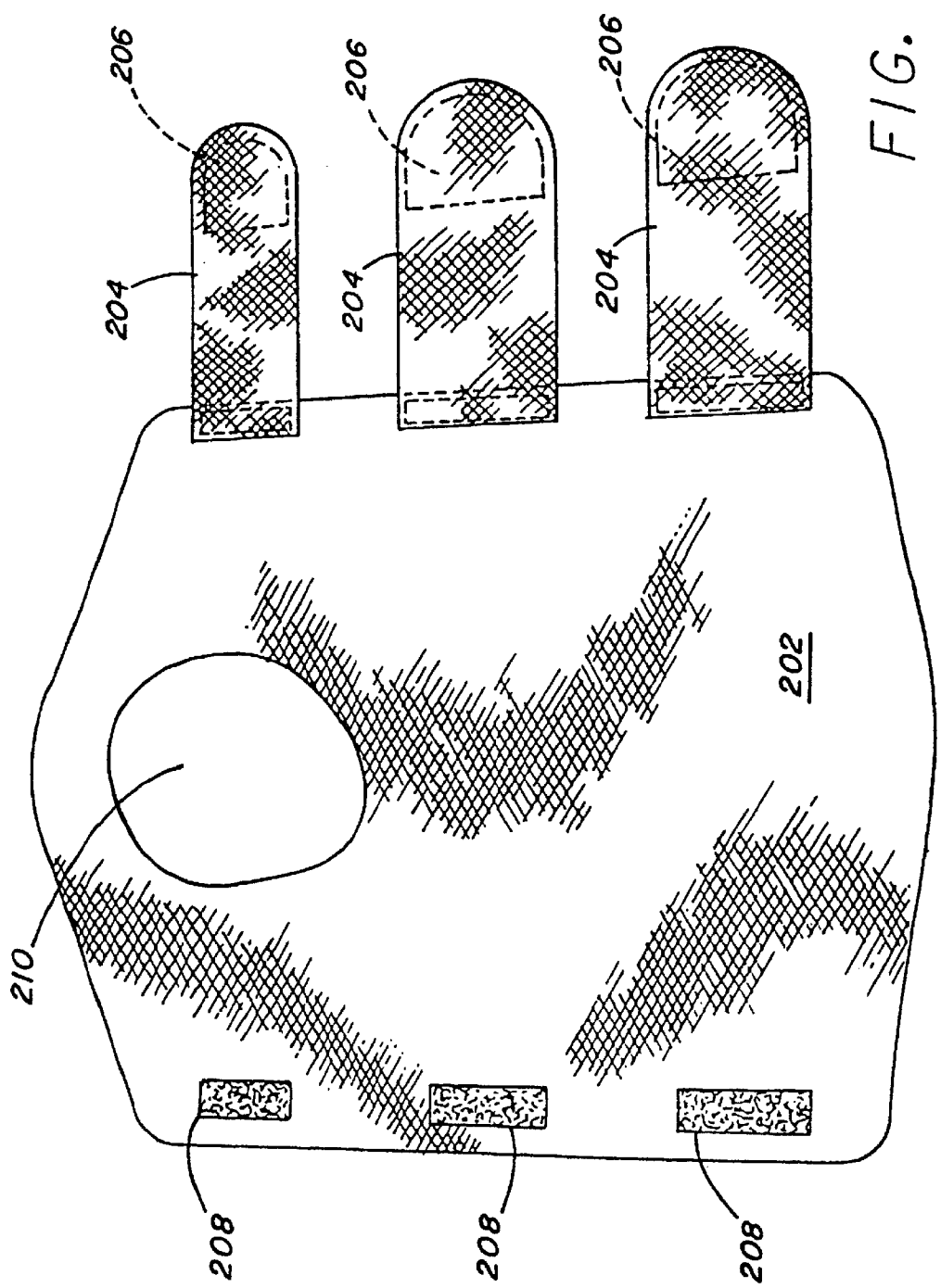
FIG. 17 shows a blank formed of doubleknit type material provided with straps.
Figure 18:
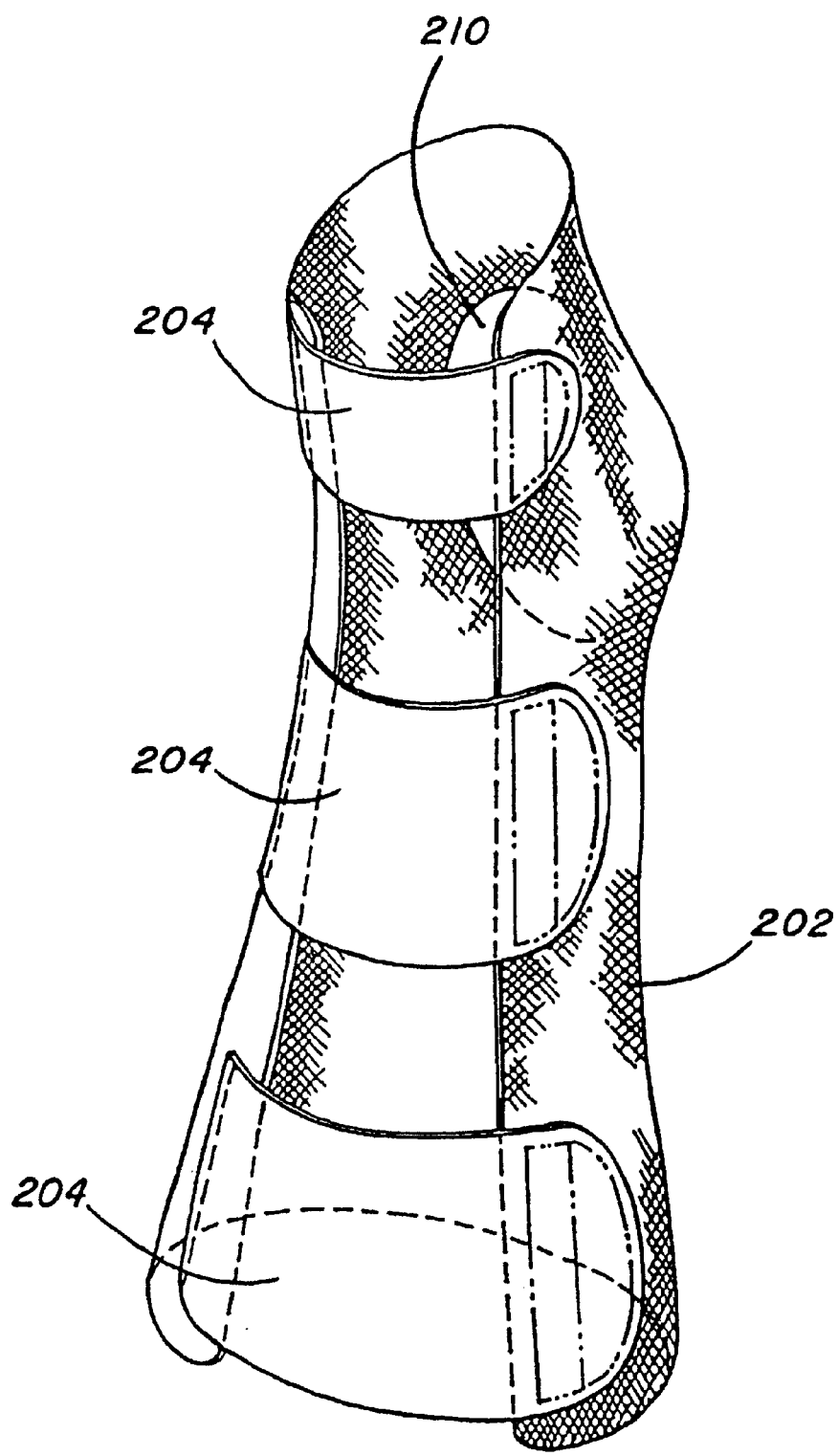
FIG. 18 shows the support or splint of FIG. 17 formed into a three-dimensional configuration.

FIG. 17 shows a flat layer 202 of doubleknit-type material, with straps 204 for securing the resultant splint or support in a three-dimensional configuration onto the wrist or forearm of the patient. The doubleknit-type material is impregnated with water-hardenable material, and sold in a water vapor impermeable package. At the time of use, it is immersed in water to initiate the hardening, and mounted on the patient, with the pads 206 on the straps mating with pads 208 on the doubleknit-type material 202. The pads may be formed of mating hook and looptype material, known as VELCRO®. The thumb of the patient extends through the opening 210. FIG. 18 shows the splint or support of FIG. 17 in a formed three-dimensional configuration, with the opening 210 extending downward in FIG. 18. Thus, the construction of FIGS. 17 and 18 results in an inexpensive, simple, and effective splint or support. A thin layer of non-impregnated soft cloth material may be provided on the side of the doubleknit material which is to engage the skin of the patient.

Now, referring back to FIG. 4 of the drawings, the dashed lines 172 represent a water vapor impermeable package for containing the orthopaedic product. This could be formed of metallized mylar, aluminum foil, or any known water vapor impermeable material, which will prevent premature activation and hardening of the urethane and the HPMC impregnated into the doubleknit material. While the water-impermeable packaging is shown with regard to FIG. 4, it is also applicable to all of the other embodiments of the invention.

Figure 19:
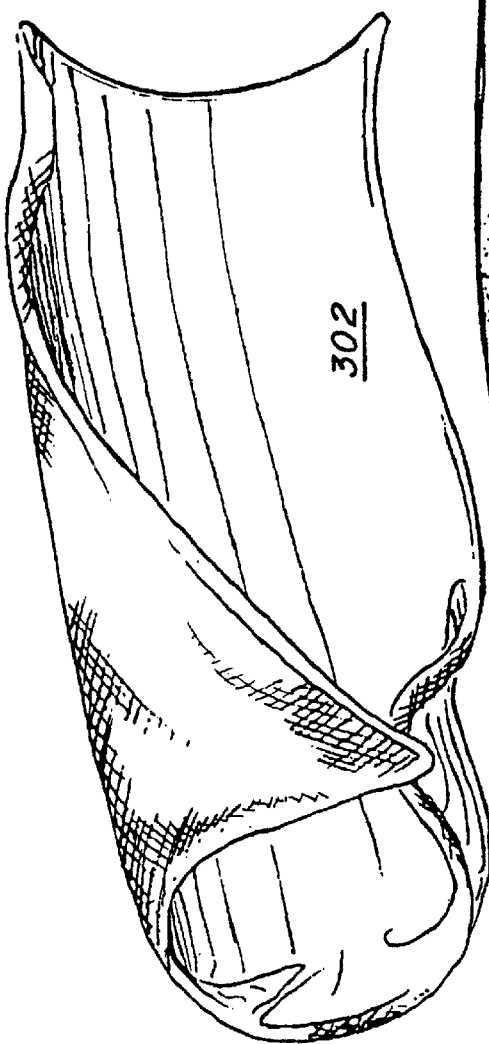
FIG. 19 shows a molded cast made from Plaster of Paris bandages prepared using a mixture of Plaster of Paris and hydroxy propyl methyl cellulose (HPMC), as disclosed in U.S. Pat. No. 3,043,298 issued to Brickman et al. on Jul. 10, 1962.

FIG. 19 shows a molded cast 302 made from Plaster of Paris bandages prepared using a mixture of a Plaster of Paris and HPMC, as disclosed in the Brickman patent. The fabric cast assembly of Brickman following hardening has a surface roughness or deviation from flatness of approximately 0.025 inch, which is relative coarse in comparison to a cast made from the doubleknit material, urethane, and HPMC, as disclosed in the current invention. As stated above, the surface roughness or deviation from flatness is the estimated depth of recesses or irregularities from a straight line or a flat plane in areas where the cast or splint is substantially flat. Furthermore, a hardened Brickman cast weighs about twice as much as a cast of comparable size that is made using urethane water hardenable material.

Figure 20:
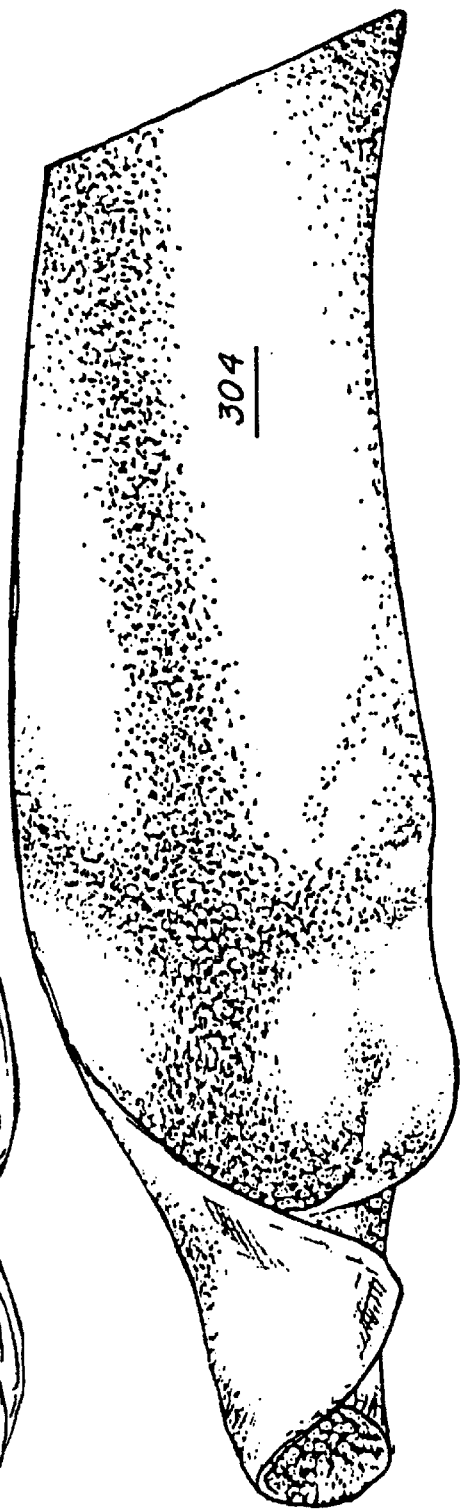
FIG. 20 shows a hardened orthopaedic support made from a curable resin coated sheet that is treated with a lubricant, as disclosed in U.S. Pat. No. 4,667,661 and U.S. Pat. No. 4,774,937, both issued to Scholz et al. as purchased from the assignee of the Scholz et al. patents.

FIG. 20 illustrates a hardened orthopaedic support 304 made from a curable resin coated sheet that is pre-lubricated, as disclosed in the Scholz patents. The Scholz curable resin coated sheet is formed of six layers of fiberglass fabric. These fiberglass fabric layers have a combined thickness of about 0.20 to 0.25 inch. Also, the Scholz resin with added lubricant has a coefficient of friction of 0.31 after wetting. Furthermore, a hardened Scholz curable resin coated sheet has a surface roughness or deviation from flatness of about 0.035 inch.

FIG. 21 shows an example of a hardened tractable orthopaedic splint or support in accordance with the present invention. The splint or support is initially formed of a doubleknit material impregnated with HPMC and urethane, is subsequently immersed in water, and is finally allowed to harden. The doubleknit-type material is about 0.15-inch thick. The smooth and velvety HPMC and urethane compound has a coefficient of friction of approximately 1.76 after wetting. The hardened orthopaedic support has a surprisingly smooth surface in comparison with the above cited prior art devices. The surface roughness or deviation from flatness of the exemplary tractable orthopaedic support is generally less than 0.010 inch.

For all of the products as described hereinabove, the doubleknit type material may be impregnated with water hardenable urethane. HPMC will also be applied to the doubleknit type material in sufficient amount to reduce the stickiness of the water hardenable urethane. The HPMC may be mixed in with the water hardenable urethane prior to impregnation, or may be applied to at least one of the outer surfaces of the doubleknit type material. Then the entire soft good product, tape or blank, is packaged in the water vapor impermeable package. When it is time to apply the product to a patient, water is supplied to the impregnated doubleknit material, and the assembly is mounted onto the part of the anatomy requiring support or splinting. With the openwork matrix of the doubleknit material, rapid and uniform penetration of the water and activation of the water hardenable material occurs. As noted above, sufficient HPMC is employed so that the wetted assembly has may be easily configured to conform to the three-dimensional shape of the injured anatomy. In the case of the soft goods type of products, straps are employed to mount the units securely on the injured portion of the anatomy, and the water hardenable compound of conforms to the configuration of the patient. Similarly, in the case of the blanks or the tapes, they are immersed in water and then applied to the injured portion of the anatomy before the hardening occurs.

Concerning the surface roughness of the various casts made from the casting materials discussed above, the surface roughness or deviation from flatness of the Plaster of Paris cast as disclosed in Brickman is approximately 0.025 inch; the surface roughness of a Scholz cast is about 0.035 inch; and the surface roughness of one illustrative-embodiment of the present invention is generally less than 0.010 inch.

Concerning the BPMC and urethane mixture in the present invention, HPMC is in practice admixed with urethane in amounts of 1 to 10 parts by weight of HPMC per 100 parts by weight of the urethane. In the preferred practice, generally about 4 part by weight of HPMC per 100 parts by weight of urethane are used.

Concerning the strength of the doubleknit-type material as compared with several layers of fiberglass fabric, certain flexural modulus tests were done, with six inch by four inch samples. In the tests, the test samples were impregnated with the same water hardenable material, were activated by water, and permitted to harden, with the same procedures being used for all samples. The test samples using the doubleknit-type material weighed about 34 grams; and the weight of the fiberglass samples, using six layers of fiberglass, was about 40½ grams, or about 22% heavier than the doubleknit-type material test samples. The strength of the doubleknit-type samples was about 71 pounds at the yield point for the hardened samples, while the yield point for the layered fiberglass test samples was about 47 pounds. Accordingly, the doubleknit-type material was nearly 50% stronger than the fiberglass samples, as well as being lighter.

Concerning the details of the test samples, the layered fiberglass samples were formed of six layers of Pinnacle Brand Fiberglass Tape. The doubleknit-type material had fiberglass top and bottom layers, and the spacer yarn was monofilament plastic, 30 denier; and the fiberglass fabric had 23 courses and 14½ wales per inch, and was 446 denier. The six layers of fiberglass fabric together were about 0.20 to 0.25-inch thick, and the doubleknit-type material was about 0.15-inch thick. Accordingly, the doubleknit-type material was thinner, stronger and lighter weight than the conventional layered fiberglass casting material.

It is noted in passing that the reaction between the water hardenable urethane material and water is exothermic, and higher temperatures occur with higher concentrations of catalyst in the urethane, with accompanying more rapid setting of the cast or splint. However, care must be taken to avoid concentrations so high that the resultant elevated temperatures may be painful or injurious to the patient. The use of HPMC as a lubricating ingredient is helpful in moderating temperature levels as it absorbs water, and the presence of this additional water keeps the temperature from rising to undesirably high levels.

It is to be understood that the foregoing detailed description and the accompanying drawings relate to preferred embodiments of the invention. Further modifications and variations of the present invention are contemplated, with products similar to doubleknit material with two surface materials and intermediate spacer filaments or threads being specifically envisioned. Also, instead of stitching, heat bonding, or the use of adhesives may be employed to hold the parts or areas of the supports together. Also, in some cases, the outer channel 42 may be dispensed with, and the straps may be secured to edges of the layered material, or overlapping edges may be provided with VELCRO type material, or eyelets or hooks and laces, to hold the support in place.

With regard to materials which may be used, it is desired that one or both of the outer layers and/or the spacer yarns or fibers of the doubleknit-type material be of high strength material, such as fiberglass, kevlar, aramids, or other high strength fibers or materials. For specific example, at least a substantial portion, such as one-quarter or one-third, of the spacer yarns or fibers may be made of fiberglass material. The spacer yarns, and one of the two outer layers may be formed of polypropylene, polyester, or nylon. Other materials and yams may also be used. More generally, it is desirable that the overall strength of the doubleknit-type fabric be relatively high, and this can be accomplished by having at least some of the fibers or yams included in the fabric be of relatively high strength material. Concerning the thickness of the doubleknit-type material, it may range from 1/16-inch thickness to ¾-inch thickness, with ⅛-inch to ⅜-inch being preferred. For a finger splint, for example, relatively thin doubleknit-type material would be used, while for a leg brace or support, much thicker material would be employed. It is further noted that the properties of the doubleknit-type casting material may be changed as desired by (1) altering filament size and/or type of surface yarns or spacer yarns, (2) changing the type of surface knits, (3) changing the density of spacer yarns, (4) interweaving stretchable yarns such as lycra to increase strength and recovery, and (5) selectively inlaying high strength fibers such as carbon, kevlar or the like. It is also noted that a flexible carrier material may be used in place of the doubleknit type material where HPMC is employed in combination with the water hardenable resin. As an example, a flexible carrier may be a fabric tape that is sufficiently porous to receive water hardenable material and water. It is also noted that flat or contoured casting blanks may be knitted in a completed form so that the steps of cutting the material and securing against fraying may be avoided. Regarding lubricating materials, additional lubricating materials may be added in addition to the HPMC, and such additional lubricating materials could include celulosic lubricating materials which may have desirable water-absorbing properties. Accordingly, the present invention is not limited to the specific embodiments described hereinabove and shown in the drawings.

What is claimed is:

1. An orthopaedic method comprising the steps of:
   a) forming an integral double layer fabric having spaced interwoven layers formed of high strength filaments and an open-work matrix of filaments interconnecting said layers;
   b) impregnating said fabric with a water-hardenable urethane under low humidity conditions, while retaining the configuration of said matrix permeable to receive water;
   c) supplying hydroxy propyl methyl cellulose (HPMC) to said fabric, as a lubricating agent to facilitate handling of the fabric following wetting;
   d) supplying additional lubricating material other than EPMC to said fabric;
   e) packaging said impregnated fabric in a water vapor impermeable package;
   f) subsequently opening said package;
   g) supplying water to said open-work matrix following opening of said package to rapidly wet said water-hardenable urethane and said HPMC; and
   h) locating the impregnated double layer fabric adjacent the injured part of the anatomy so that said impregnated fabric conforms to the configuration of the anatomy; whereby (1) the open-work matrix of said double layer fabric facilitates rapid and uniform impregnation by the water-hardenable urethane, and uniform penetration of the water, and also provides firm support resulting from the hardening of the water-hardenable urethane in the open-work matrix; (2) the HPMC reduces the stickiness of the urethane when wetted; (3) and smooth outer surfaces are produced following hardening.

2. An orthopaedic method as defined in claim 1 wherein said method includes providing a layer of high strength glass fiber material to increase the strength of said fabric.

3. An orthopaedic method as defined in claim 1 wherein said method includes providing a layer of padding on at least one side of said impregnated fabric, said impregnated fabric may be located with said padding layer being adjacent to the skin of the injured part of the anatomy to protect the skin.

4. An orthopaedic method as defined in claim 1 wherein said method includes forming an assembly including soft goods structure for enclosing said fabric and for holding said assembly onto the portion of the anatomy requiring support.

5. An orthopaedic method as defined in claim 1 wherein said step of applying HPMC to said fabric includes applying said HPMC on at least one outer surface of said fabric in sufficient amount to provide a smooth and velvety feel when wetted, and smooth outer surfaces when hardened.

6. An orthopaedic method as defined in claim 1 wherein said step of applying HPMC includes admixing said urethane with said HPMC to form a urethane and HPMC mixture, and said step of impregnating said fabric includes impregnating said fabric with said urethane and KPMC mixture.

7. A hardenable orthopaedic assembly comprising:
   an active layer formed of a double layer fabric having spaced interwoven layers and an open-work matrix of fibers inter-connecting said interwoven layers; said interwoven layers being independently movable with respect to each other, within the limits of said inter-connecting fibers, for ease in three-dimensional draping around the anatomy;
   said active layer being impregnated with water hardenable urethane, and having hydroxy propyl methyl cellulose (HPMC) and additional different lubricating material supplied thereto; and
   a water vapor impermeable packaging enclosing said impregnated double layer fabric;
   whereby the open-work matrix of said active double layer fabric facilitates rapid and uniform impregnation by said urethane, and subsequent uniform penetration of water, and also provides firm support resulting from the hardening of said urethane in the open-work matrix; and said HPMC and additional lubricating material reduces the stickiness of said urethane when wetted.

8. A hardenable orthopaedic assembly as defined in claim 7 further comprising a non-impregnated layer of soft material secured to one side of said double layer fabric for engagement with a patient's skin.

9. The hardenable orthopaedic assembly as claimed in 7, wherein said double layer fabric has outer surfaces, and said HPMC is applied to at least one outer surface of said double layer fabric.

10. The hardenable orthopaedic assembly as defined in claim 7, wherein said urethane is admixed with said APMC to form a urethane and lubricating material mixture, and said active layer is a flexible carrier.

11. The hardenable orthopaedic assembly as defined in claim 10, wherein said mixture includes approximately 1 to 10 parts by weight of lubricating material per 100 parts by weight of the urethane.

12. The hardenable orthopaedic assembly as defined in claim 10, wherein said urethane and HPMC mixture includes in the order of 4 parts by weight of lubricating material per 100 parts by weight of the urethane.

13. A hardenable orthopaedic cast or support comprising:
    a flexible carrier;
    water hardenable resin impregnated into said carrier;
    said cast or support including hydroxy propyl methyl cellulose (HPMC) included with said water hardenable resin to decrease the stickiness of said resin following the addition of water.

14. A hardenable orthopaedic cast or support as defined in claim 13 wherein said cast or support includes additional lubricating material in addition to HPMC.

15. A cast or support as defined in claim 13 wherein said HPMC is mixed into said resin.

16. A cast or support as defined in claim 13 wherein said HPMC is added to the outer surface of said resin.

17. A cast or support as defined in claim 13 wherein said flexible carrier is a doubleknit fabric.

18. A hardenable orthopaedic cast or support as defined in claim 13 further comprising a non-impregnated layer of soft material secured to one side of said flexible carrier for engagement with a patient's skin.

19. A hardenable orthopaedic cast or support as defined in claim 13 further comprising a water impermeable layer on at least one side of said flexible carrier.

* * * * *

UNITED STATES PATENT AND TRADEMARK OFFICE
CERTIFICATE OF CORRECTION

PATENT NO.    : 6,461,317 B1                                      Page 1 of 1
DATED         : October 8, 2002
INVENTOR(S)   : Tracy E. Grim et al.

It is certified that error appears in the above-identified patent and that said Letters Patent is hereby corrected as shown below:

<u>Column 13,</u>
Line 25, please delete "EPMC" and insert -- HPMC --.

Signed and Sealed this

Twenty-first Day of January, 2003

JAMES E. ROGAN
*Director of the United States Patent and Trademark Office*